United States Patent [19]
Carnes et al.

[11] Patent Number: 4,569,231
[45] Date of Patent: Feb. 11, 1986

[54] MULTIPLE FREQUENCY ANNULAR TRANSDUCER ARRAY AND SYSTEM

[75] Inventors: Ronald C. Carnes, Folsom; Stockton M. Miller-Jones, Rancho Cordova, both of Calif.

[73] Assignee: General Electric Company, Milwaukee, Wis.

[21] Appl. No.: 629,225

[22] Filed: Jul. 9, 1984

[51] Int. Cl.⁴ ............................................. G01N 29/00
[52] U.S. Cl. ............................................. 73/626
[58] Field of Search ................. 73/626, 625, 628, 620; 128/660

[56] References Cited

U.S. PATENT DOCUMENTS

| | | | |
|---|---|---|---|
| 3,292,018 | 12/1966 | Clynes | 73/628 |
| 4,155,259 | 5/1979 | Engeler | 73/626 |
| 4,241,611 | 12/1980 | Specht et al. | 73/626 |
| 4,459,853 | 7/1984 | Miwa et al. | 73/626 |

Primary Examiner—Stephen A. Kreitman
Attorney, Agent, or Firm—Flehr, Hohbach, Test, Albritton & Herbert

[57] ABSTRACT

A scanning system having a variable field of imaging uses a transducer array including a central element and one or more annular elements concentric therewith. The central element is energized at a first frequency for near field imaging, and the one or more annular elements are energized at lower frequencies for intermediate and far field imaging. Electrical signals generated by the transducer elements in response to reflected ultrasonic waves are demodulated to form in-phase and quadrature phase demodulated signals, and the in-phase and quadrature phase electrical signals are then summed to provide an enhanced image signal.

7 Claims, 5 Drawing Figures

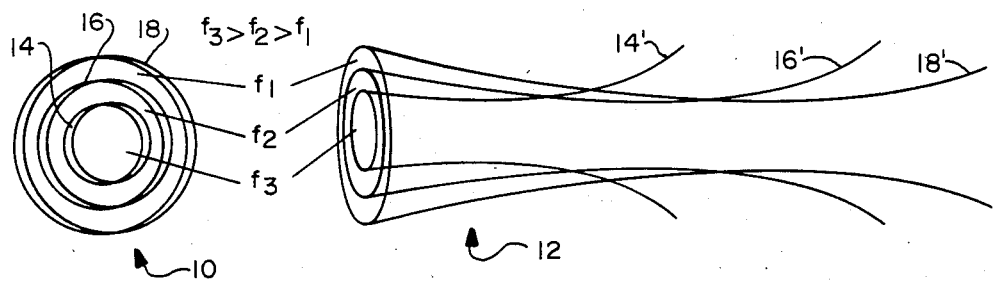
FIG. — 1
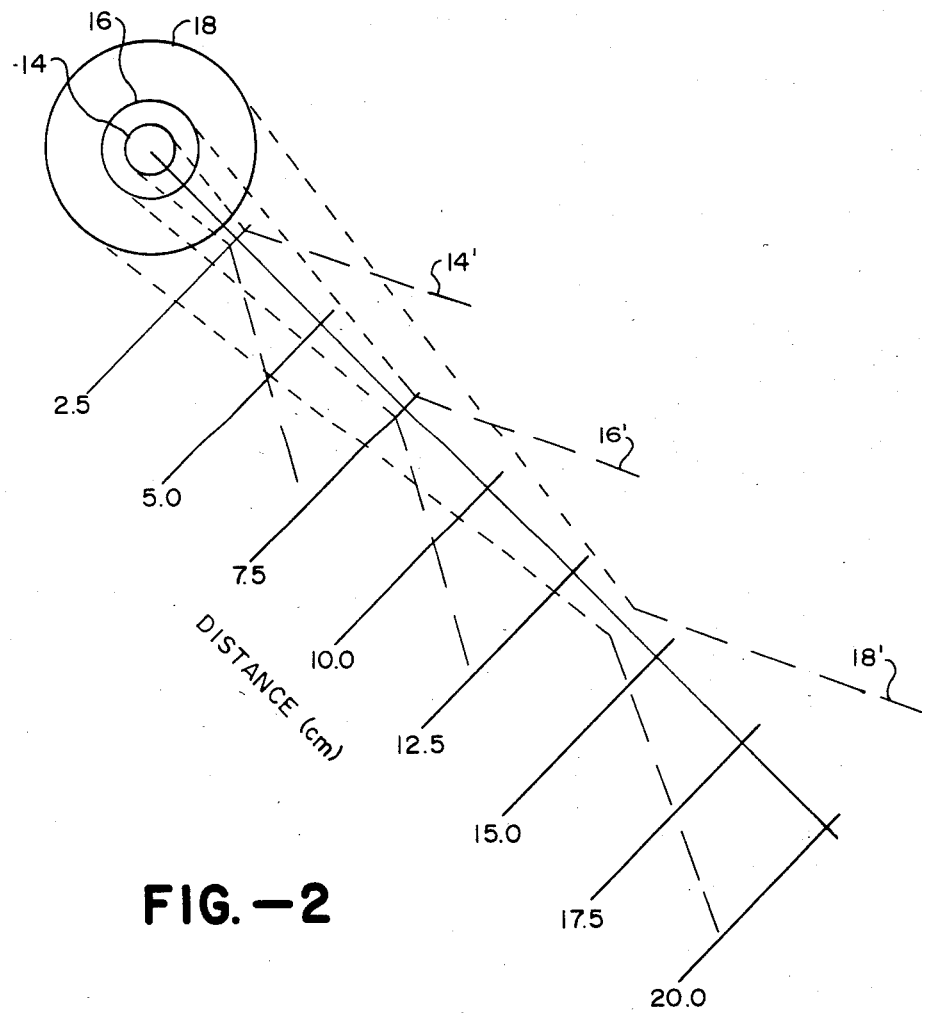
FIG. — 2

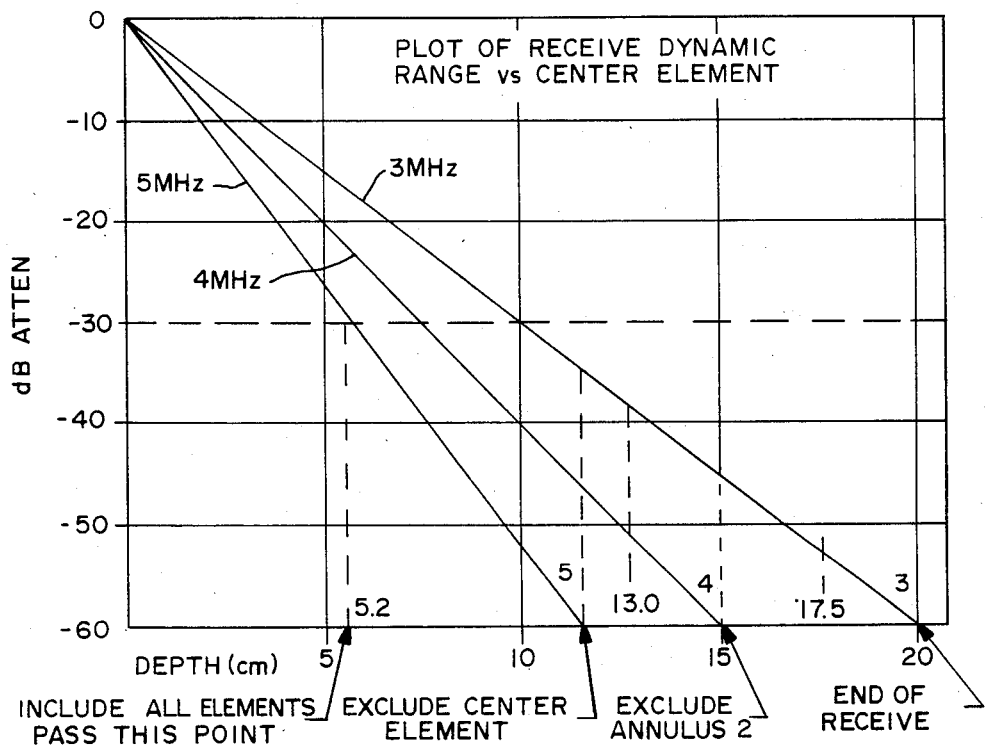
FIG. — 3
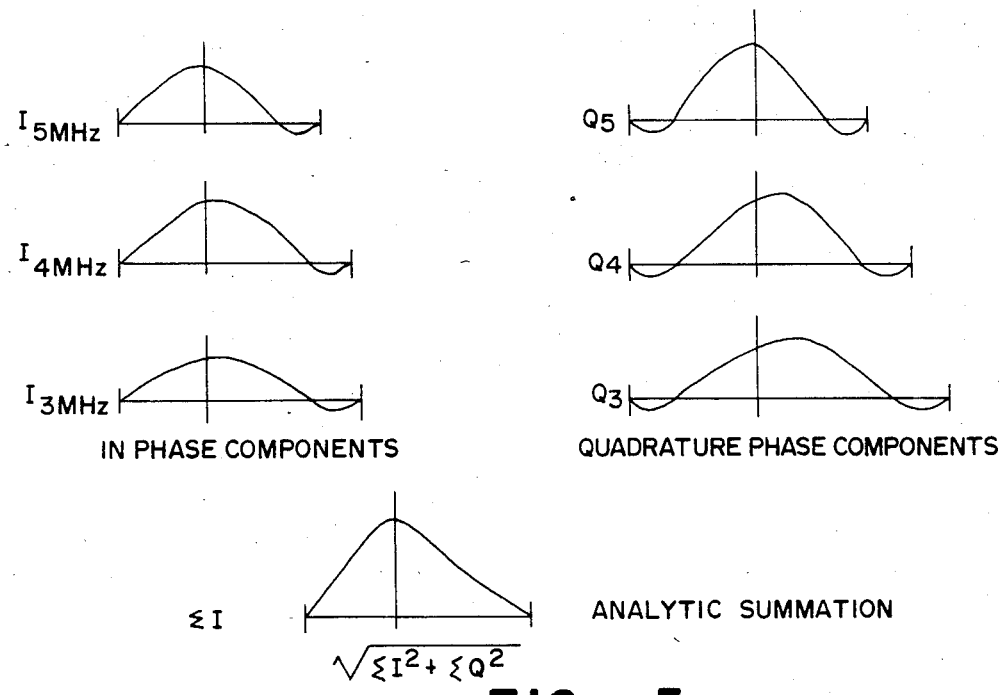
FIG.—5

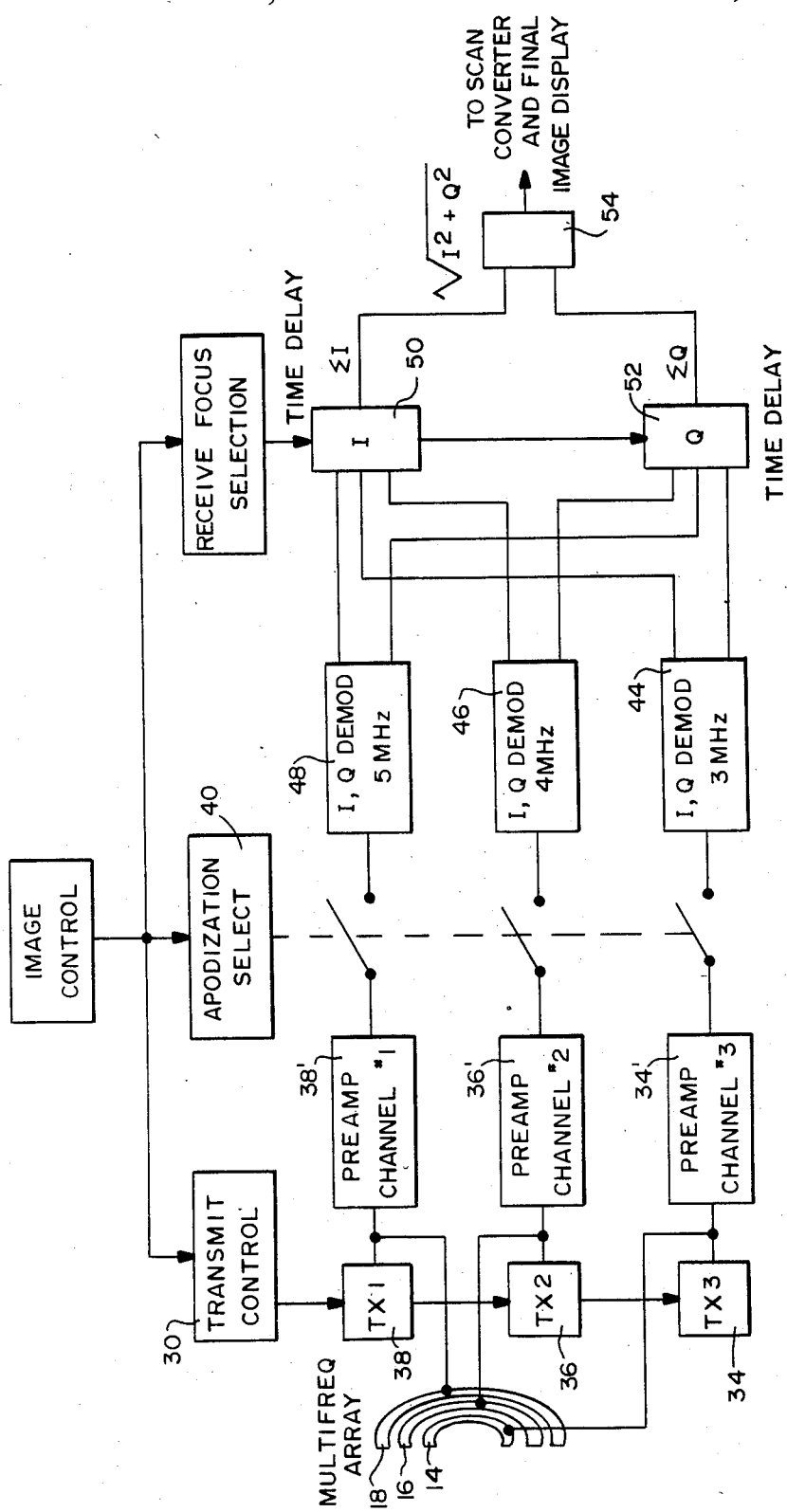
FIG.—4

MULTIPLE FREQUENCY ANNULAR TRANSDUCER ARRAY AND SYSTEM

This invention relates generally to ultrasound scanning and imaging systems, and more particularly, the invention relates to a multiple frequency annular transducer array and scanning system having a large usable depth of field.

Ultrasound systems as used for medical diagnostic purposes have become extremely specialized. Further, the ultrasound probes which are used in the systems typically have fixed apertures and depths of focus, thus requiring the user to maintain a plurality of probes and to exchange the probes for different resolutions, penetration, and anatomical access for given imaging modality.

Resolution and penetration are complex functions of frequency, aperture size, and dispersive interactions of the sound beam with tissue. For a given depth of interest in the body, it is desirable to utilize as high a frequency as possible to provide the best resolution. However, the signal to noise ratio limits the given usuable bandwith for a given depth. This is due to the attenuation of ultrasound by the body being approximately a first order dependence on the frequency and a first order dependence on depth in the body.

In accordance with the present invention a multiple frequency annular transducer array having a large usable depth of field is provided. Preferably, the constituitive radii and frequencies are chosen such that the near field/far field transitions for the individual elements lie just beyond the zone of imaging for inclusion of that element. For depth zones further in range than that capable being imaged by the more centered elements, the centered elements are excluded from the receive analog chain to eliminate their contribution to the noise voltage.

Advantageously, the multiple frequency annular array can be used in a base band system as described in U.S. Pat. No. 4,155,259. Such a system has heretofore been used with a phased array of transducer elements operated at a single frequency. In such a system both in-phase and quadrature phase demodulation are employed to isolate the desired frequency from other frequencies. Thus, by separately demodulating frequencies of interest, the demodulated signals can then be summed so that the multiple frequency annular array functions as a single crystal. Selection of one or more of the annular crystals will depend on the desired depth of field and the ranges of the individual cyrstals.

The invention and objects and features thereof will be more readily apparent from the following detailed description and appended claims when taken with the drawing, in which:

FIG. 1 is a persepctive view of a three element annular transducer array in accordance with one embodiment of the invention and beam patterns therefrom.

FIG. 2 is a plot of beam patterns versus depth for the transducer array of FIG. 1.

FIG. 3 is a plot of dynamic range of the transducer elements in FIG. 1 versus depth.

FIG. 4 is a functional block diagram of a system for using the transducer array of FIG. 1.

FIG. 5 is a plot of demodulated signals illustrating operation of the system of FIG. 4.

Referring now to the drawings, FIG. 1 is a schematic representation of a transducer array shown generally at 10 and beam patterns shown generally at 12 generated by the transducer array. In this embodiment the array 10 comprises three concentric elements 14, 16, and 18 formed in a surface of a piezoelectric crystal with the crystal functioning as a common ground plane. The radii of the elements are 0.4 cm, 0.813 cm, and 1.25 cm, respectively. Suitable time delay of transmitted and received ultrasonic waves is provided by a conventional lens (not shown). The inner element 14 is operated at the highest frequency $f_3$, the next element 16 is operated at a lower frequency $f_2$, and the outer element 18 is operated at the lowest frequency $f_1$. In the illustrative embodiment the frequencies of $f_1$, $f_2$ and $f_3$ are respectively 3 MHz, 4 MHz, and 5 MHz. The inner element 14 operating at the highest frequency generates a beam pattern 14' which converges to a focal point at 2.5 cm and becomes divergent thereafter as illustrated in FIG. 2. The intermediate beam pattern 16' converges to a focal point at 7.5 cm and becomes divergent thereafter, and the lowest frequency beam 18' converges to a focal point at approximately 14 cm and becomes divergent thereafter. Accordingly, by using one or more of the transducer elements the transducer array can be used over an extended depth of field from the body wall to a depth of approximately 20 cm.

This is further illustrated in FIG. 3 which is a plot of dynamic range of each transducer element versus depth. In this plot the noise floor is taken to be −60 db. From the body wall to a depth of 5.2 cm the 5 MHz beam generated by the center element 14 is employed as the other two beams lack sufficient resolution to contribute to imaging. From 5.2 cm to 12 cm all three transducer elements are utilized in forming the ultrasonic beam. Beyond 12 cm the center element 14 loses sufficient sensitivity to contribute significantly to the received signal strength relative to the noise floor at −60 db. From a depth of 12 cm to 15 cm, the two annular elements 16 and 18 are utilized to form the ultrasonic beam, and beyond 15 cm only the outer annular element 18 operating at 3 MHz is employed. Beyond 20 cm none of the beams has sufficient sensitivity to be distinguishable from the noise floor.

A direct summation of the received signals from two or more of the beams produces degraded resolution because the resultant phase superposition from each of the contributing elements produces ambiguous phase reversals that cause an ill defined pulse arrival time. However, in accordance with the invention the multielement concentric transducer array is employed in a base band system as disclosed in U.S. Pat. No. 4,155,259, supra. FIG. 4 is a functional block diagram of such a system for the described three element array. Transmission of ultrasonic beams by one or more of the three elements is effected by the transmit control 30 which controls the pulsing and wave shape circuitry 34, 36, and 38 for each of the elements. The received signals from each of the elements are processed by preamplifier circuitry 34', 36' and 38', and the processed signals selected by the apodization select circuitry 40, depending on the depth to be imaged, are then passed through in-phase and quadrature phase demodulators 44, 46, and 48. As disclosed in U.S. Pat. No. 4,155,259, supra, the demodulator circuitry permits coherent addition of the received echo signals which are in-phase summed and quadrature phase summed at 50 and 52. The in-phase and quadrature sums are then combined at 54 as a composite reflected beam signal which is then transmitted to the scan converter for final image display.

FIG. 5 is plots of the in-phase and quadrature phase components and the summed in-phase and quadrature phase components derived from the circuitry of FIG. 4. As illustrated, the three demodulated signals can be combined constructively to realize an improved reflected beam signal.

A multielement annular transducer array as described permits improved imaging in a near field, an intermediate field, and a far field by selectively combining the reflected beam signals from each of the transducer elements which are operated for particular depths of focus to produce the best resolution and penetration given the constraint of frequency dependent attenuation of soft tissue. Thus, a high quality image is provided over an extended depth of field.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. An ultrasound system having variable depth of field comprising
    an array of transducer elements including a center element and at least one annular element concentric therewith,
    means connected to said array of elements for selectively energizing said elements at different frequencies to generate ultrasonic beams having different depths of focus, said elements receiving reflected ultrasonic waves in response to the generated ultrasonic beams,
    demodulation means operably connected to receive electrical signals from said array of transducer elements in response to the received reflected ultrasonic waves, said demodulation means demodulating said electrical signals form in-phase and quadrature phase demodulation signals, and
    summing means connected to said demodulation means for receiving and summing said in-phase and said quadrature phase signals to form an enhanced reflected signal for imaging.

2. The ultrasound system as defined by claim 1 wherein said center element is energized at a frequency for near field imaging and said at least one annular element is energized at a lower frequency for far field imaging.

3. The ultrasound system as defined by claim 2 wherein said array of transducer elements includes at least two concentric annular elements, the larger annular element being energized at a lower frequency than the smaller annular element whereby said smaller element is energized for intermediate field imaging and said larger annular element is energized for far field imaging.

4. The ultrasound system as defined by claim 3 wherein said central element is operated at 5 MHz, said smaller annular element is operated at 4 MHz, and said larger annular element is operated at 3 MHz.

5. The ultrasound system as defined by claim 4 wherein said array of transducer elements is formed in one surface of a piezoelectric crystal, said piezoelectric crystal functioning as a common ground plane for all of said elements.

6. The ultrasound system as defined by claim 1 wherein said array of transducer elements if formed in one surface of a piezoelectric crystal, said piezoelectric crystal functioning as a common ground plane for all of said elements.

7. A method of imaging a body by an ultrasound scanner comprising the steps of
    providing a transducer array including a piezoelectric crystal having a central transducer element formed in one surface and at least a first annular transducer element formed in said one surface and concentric with said central transducer element,
    selectively energizing said central element at a first frequency for near field imaging and selectively energizing said first annular element at a second frequency for far field imaging, said second frequency being lower than said first frequency, and energizing both of said central element and said first annular element for imaging between said near field and said far field,
    generating electrical signals in response to reflected ultrasonic waves received by said transducer elements,
    demodulating said generated electrical signals to obtain in-phase and quadrature phase demodulated signals, and
    summing said in-phase and quadrature phase electrical signals to form an enhanced image signal.

* * * * *